United States Patent [19]

Owerbach

[11] Patent Number: 5,059,519

[45] Date of Patent: * Oct. 22, 1991

[54] OLIGONUCLEOTIDE PROBES FOR THE DETERMINATION OF THE PROCLIVITY FOR DEVELOPMENT OF AUTOIMMUNE DISEASES

[75] Inventor: David Owerbach, Houston, Tex.

[73] Assignee: University of Massachusetts Medical School, Worcester, Mass.

[*] Notice: The portion of the term of this patent subsequent to Oct. 23, 2007 has been disclaimed.

[21] Appl. No.: 206,054

[22] Filed: Jun. 10, 1988

Related U.S. Application Data

[63] Continuation-in-part of Ser. No. 880,857, Jul. 1, 1986, Pat. No. 4,965,189.

[51] Int. Cl.$^5$ .................... C12Q 1/68; C07H 15/12
[52] U.S. Cl. ............................... 435/6; 536/27
[58] Field of Search ........................ 435/6; 536/27

[56] References Cited

PUBLICATIONS

Spies et al., PNAS 82 5165–5169 (1985).
Boss et al. Proc. Natl. Acad. Sci. 81 5199–5203 (1984).
Gustafson et al. EMBOJ 3 1655–1661 (1984).
Maniatis et al. Molecular Cloning (1982) Cold Spring Harbor Press, Cold Spring.
Long et al. EMBOJ 2 (3) 389–394 (1983).
Angelini et al. Proc. Natl. Acad. Sci. 83 4489–4493 (1986).
Larhammor et al. Proc. Natl. Natl. Acad. Sci 82 1475–1479 (1985).
Larhammer et al. Proc. Natl. Acad. Sci. 80 7313–7317, 1983.
Owerbach et al., Immunogenetics 24: 41–46 (1986).

*Primary Examiner*—Robert A. Wax
*Assistant Examiner*—Scott Chambers
*Attorney, Agent, or Firm*—Sprung Horn Kramer & Woods

[57] ABSTRACT

DQ beta gene oligonucleotides consisting essentially of the sequence GGCCGCCTGCCGCCGAG or of the sequence GCTGGGGCTGCCTGCCG and the use of such oligonucleotides in a method for assaying for a polymorphic region associated with Type I diabetes mellitus in humans.

2 Claims, 10 Drawing Sheets

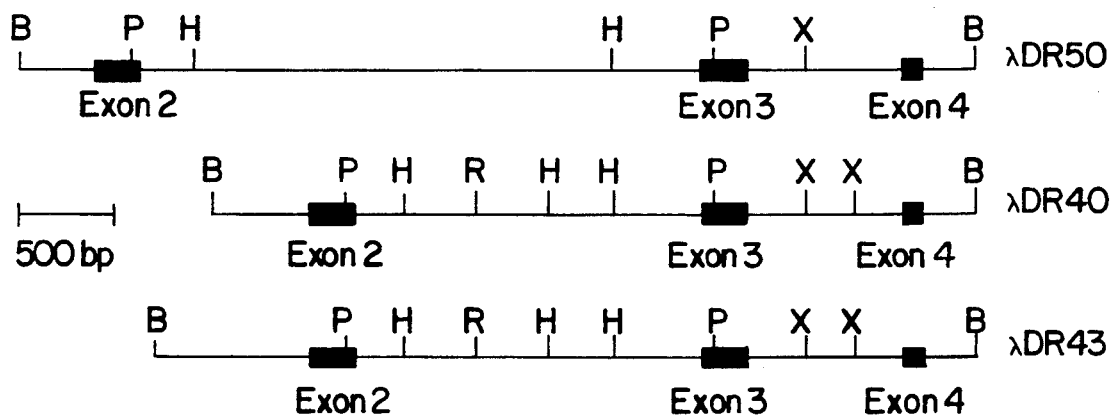

| | 101 | 102 | 103 | 104 | 105 | 106 | 107 | 108 | 109 | 110 | 111 | 112 | 113 | 114 | 115 | 116 | 117 | 118 | 119 | 120 | 121 | 122 | 123 | 124 | 125 |
|---|---|---|---|---|---|---|---|---|---|---|---|---|---|---|---|---|---|---|---|---|---|---|---|---|---|
| λDR5.0 | Val | Tyr | Pro | Ala | Lys | Thr | Gln | Pro | Leu | Gln | His | His | Asn | Leu | Leu | Val | Cys | Ser | Val | Asn | Gly | Phe | Tyr | Pro | Gly |
| λDR4.3 | — | — | — | Ser | — | — | — | — | — | — | — | — | — | — | — | — | — | — | — | Ser | — | — | — | — | — |
| λDR4.0 | — | — | — | Ser | — | — | — | — | — | — | — | — | — | — | — | — | — | — | — | Ser | — | — | — | — | — |
| 2918.4 | — | — | — | — | — | — | — | — | — | — | — | — | — | — | — | — | — | — | — | — | — | — | — | — | — |
| pII-β-1 | — | — | — | Ser | — | — | — | — | — | — | — | — | — | — | — | — | — | — | — | Ser | — | — | — | — | — |
| pII-β-3 | — | — | — | Ser | — | — | — | — | — | — | — | — | — | — | — | — | — | — | — | Ser | — | — | — | — | — |
| pII-β-4 | — | — | — | Asn | — | — | — | — | — | — | — | — | — | — | — | — | — | — | — | Asn | — | — | — | — | — |
| DR2/2 | — | — | — | Ser | — | — | — | — | — | — | — | — | — | — | — | — | — | — | — | Ser | — | — | — | — | — |

| | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 | 149 | 150 |
|---|---|---|---|---|---|---|---|---|---|---|---|---|---|---|---|---|---|---|---|---|---|---|---|---|---|
| λDR5.0 | Ser | Ile | Glu | Val | Arg | Trp | Phe | Arg | Asn | Gly | Gln | Glu | Glu | Lys | Thr | Gly | Val | Val | Ser | Thr | Gly | Leu | Ile | Gln | Asn |
| λDR4.3 | — | — | — | — | — | — | — | — | — | — | — | — | — | — | Ala | — | — | — | — | — | — | — | — | — | — |
| λDR4.0 | — | — | — | — | — | — | — | — | — | — | — | — | — | — | Ala | — | — | — | — | — | — | — | — | — | — |
| 2918.4 | — | — | — | — | — | — | — | — | — | — | — | — | — | — | — | — | — | — | — | — | — | — | — | — | — |
| pII-β-1 | — | — | — | — | — | — | — | — | — | — | — | — | — | — | Ala | — | — | — | — | — | — | — | — | — | — |
| pII-β-3 | — | — | — | — | — | — | — | — | — | — | — | — | — | — | Ala | — | — | — | — | — | — | — | His | — | — |
| pII-β-4 | — | — | — | — | — | — | — | Leu | — | — | — | — | — | Gly | — | — | Gly | — | — | — | — | — | — | His | — |
| DR2/2 | — | — | — | — | — | — | — | — | — | — | — | — | — | — | Ala | — | — | — | — | — | — | — | — | Asp | — |

| | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 |
|---|---|---|---|---|---|---|---|---|---|---|---|---|---|---|---|---|---|---|---|---|---|---|---|---|---|
| λDR5.0 | Gly | Asp | Trp | Thr | Phe | Gln | Thr | Leu | Val | Met | Leu | Glu | Thr | Val | Pro | Arg | Ser | Gly | Glu | Val | Tyr | Thr | Cys | Gln | Val |
| λDR4.3 | — | — | — | — | — | — | — | — | — | — | — | — | — | — | — | — | — | — | — | — | — | — | — | — | — |
| λDR4.0 | — | — | — | — | — | — | — | — | — | — | — | — | — | — | — | — | — | — | — | — | — | — | — | — | — |
| 2918.4 | — | — | — | — | — | — | — | — | — | — | — | — | — | — | — | — | — | — | — | — | — | — | — | — | — |
| pII-β-1 | — | — | — | — | — | — | — | — | — | — | — | — | — | Phe | — | — | — | — | — | — | — | — | — | — | — |
| pII-β-3 | — | — | — | — | — | — | — | — | — | — | — | — | — | — | — | — | — | — | — | — | — | — | — | — | — |
| pII-β-4 | — | — | — | — | — | — | — | Leu | — | — | — | — | — | — | — | — | Gly | — | — | — | — | — | — | — | — |
| DR2/2 | — | — | — | — | — | — | — | — | — | — | — | — | — | — | Ala | — | — | — | — | — | — | — | — | — | — |

| | 176 | 177 | 178 | 179 | 180 | 181 | 182 | 183 | 184 | 185 | 186 | 187 | 188 | 189 | 190 | 191 | 192 | 193 | 194 | 195 | 196 | 197 | 198 | 199 | 200 |
|---|---|---|---|---|---|---|---|---|---|---|---|---|---|---|---|---|---|---|---|---|---|---|---|---|---|
| λDR5.0 | Glu | His | Pro | Ser | Leu | Thr | Ser | Pro | Leu | Thr | Val | Glu | Trp | Arg | Ala | Arg | Ser | Glu | Ser | Ala | Gln | Ser | Lys | Met | Leu |
| λDR4.3 | — | — | — | — | Met | Met | — | — | — | — | — | Gln | — | Ser | — | — | — | — | — | — | — | — | — | — | — |
| λDR4.0 | — | — | — | — | Val | — | — | — | — | — | — | — | — | — | — | — | — | — | — | — | — | — | — | — | — |
| 2918.4 | — | — | — | — | Val | — | — | — | — | — | — | — | — | — | — | — | — | — | — | — | — | — | — | — | — |
| pII-β-1 | — | — | — | — | Val | — | — | — | — | — | — | — | — | — | — | — | — | — | — | — | — | — | — | — | — |
| pII-β-3 | — | — | — | — | Val | — | — | — | — | — | — | — | — | Ser | — | — | Ser | — | — | — | — | — | — | — | — |
| pII-β-4 | — | — | — | — | Val | Met | — | — | — | — | — | — | — | — | — | — | — | — | — | — | — | — | — | — | — |
| DR2/2 | — | — | — | — | Val | — | — | — | — | — | — | — | — | — | — | — | — | — | — | — | — | — | — | — | — |

FIG.3c

| | 201 | 202 | 203 | 204 | 205 | 206 | 207 | 208 | 209 | 210 | 211 | 212 | 213 | 214 | 215 | 216 | 217 | 218 | 219 | 220 | 221 | 222 | 223 | 224 | 225 |
|---|---|---|---|---|---|---|---|---|---|---|---|---|---|---|---|---|---|---|---|---|---|---|---|---|---|
| | Ser | Gly | Val | Gly | Gly | Phe | Val | Leu | Gly | Leu | Leu | Phe | Leu | Gly | Ala | Gly | Leu | Phe | Ile | Tyr | Phe | Arg | Asn | Gln | Lys |
| λDR5.0 | — | — | — | — | — | — | — | — | — | — | — | — | — | — | — | — | — | — | — | — | — | — | — | — | — |
| λDR4.3 | — | — | — | — | — | — | — | — | — | — | — | — | — | — | — | — | — | — | — | — | — | — | — | — | — |
| λDR4.0 | — | — | — | — | — | — | — | — | — | — | — | — | — | — | — | — | — | — | — | — | — | — | — | — | — |
| 2918.4 | — | — | — | — | — | — | — | — | — | — | — | — | — | — | — | — | — | — | — | — | — | — | — | — | — |
| DRβ-1 | — | — | — | — | — | — | — | — | — | — | — | — | — | — | — | — | — | — | — | — | — | — | — | — | — |
| pII-β-3 | — | — | — | — | — | — | — | — | — | — | — | — | — | — | — | — | — | — | — | — | — | — | — | — | — |
| pII-β-4 | — | — | — | — | — | — | — | — | — | — | — | — | — | — | — | — | — | — | — | — | — | — | — | — | — |
| DR2/2 | — | — | — | — | — | — | — | — | — | — | — | — | — | — | — | — | — | — | — | — | — | — | — | — | — |

| | (226) | 227 | 228 | 229 | 230 | 231 | 232 | 233 | 234 | 235 | 236 | 237 |
|---|---|---|---|---|---|---|---|---|---|---|---|---|
| | Gly | His | Ser | Gly | Leu | Gln | Pro | Thr | Gly | Phe | Leu | Ser |
| λDR5.0 | — | — | — | — | — | — | — | — | — | — | — | — |
| λDR4.3 | — | — | — | — | — | — | — | — | — | — | — | — |
| λDR4.0 | — | — | — | — | — | — | — | — | — | — | — | — |
| 2918.4 | — | — | — | — | — | — | — | — | — | — | — | — |
| DRβ-1 | — | — | — | — | — | — | Arg | — | — | — | — | — |
| pII-β-3 | — | — | — | — | — | Pro | — | — | — | — | — | — |
| pII-β-4 | — | — | — | — | — | — | — | — | — | — | — | — |
| DR2/2 | — | — | — | — | — | — | — | — | — | — | — | — |

PROBE A

GTACCCCTGGGGAAGCAGTCATGCCTGCCAAGCAGGAGAGGCTGTCCCTCTTTGAACCTCCCCATGATGT
CACAAGTCGGGGTCACCTGCTGTCTGTGGGCTCCAGGCCCTGCCTCTGGGACAGAGACTGAGTTTCTGGTAC

PROBE B

TCTAGAAACACCTGTACCTCCTGGGAGAAGCAGTCTGCCTGCCAAGCAGGAGAGGCTGTCCCTCTTT
TGAACCTCCCCATGATGTCACAGGTCAGGGTCACCCTCACCCTCCCCGGGCTCCAGGCACTGCCTCTGG
GTCTGAGACTGAGTTTCTGGTGCTGTTGATCTGAGTATTGTTGTGATCTGGGAAGAGGAGAAGTG
TAGGGACCTTCCTGACATGAGGGGAGTCCAATCTCAGCTCTGCCTTTTATTAGCTCTGTCACTCTAGA

OLIGONUCLEOTIDE PROBES FOR THE DETERMINATION OF THE PROCLIVITY FOR DEVELOPMENT OF AUTOIMMUNE DISEASES

CROSS REFERENCE TO RELATED APPLICATION

This application is a continuation-in-part application of application Ser. No. 06/880,857, filed July 1, 1986, now U.S. Pat. No. 4,965,189, issued Oct. 23, 1990.

BACKGROUND OF THE INVENTION

1. Field of the Invention

The present invention concerns oligonucleotide probes for the determination of the proclivity in human individuals to develop autoimmune diseases, particularly insulin-dependent diabetes mellitus (IDDM).

2. Background Information

Diabetes mellitus (DM) a syndrome characterized by insufficient insulin secretion, hyperglycermia and a propensity to develop universal microargiopathy, neuropathy and atherosclerosis, is a common condition affecting 1 to 2 per cent of Caucasian populations. Insulin-dependent diabetes mellitus (IDDM) (Type 1 diabetes) comprises 10 to 15 per cent of all DM sufferers and is characterized by a selective pancreatic beta cell destruction, a very low, if any, insulin secretion, an absolute requirement for exogenous insulin, a low age of onset (although cases do occur in all ages) and a high percentage of autoantibodies directed against antigenic determinants of the beta-cells. IDDM has been shown to be associated with two alleles (HLA-DR3 and HLA-DR4) of the HLA-D/DR locus on chromosome 6. While these two alleles are present in 97% of IDDM patients, they are also present in 50% of the background population (Caucasian), and, therefore, these markers as serologically defined are not highly specific for the disease.

Essential to an understanding of the etiology of insulin-dependent diabetes mellitus (IDDM) is a more complete definition of the specific genetic susceptibilities. In family studies, the individuals at highest risk for IDDM are siblings who share both HLA haplotypes with the diabetic proband; their lifetime risk for disease is in the order of 12-24% (A. N. Gorsuch, K. M. Spencer, J. Lister, E. Wolf, G. M. Bottazzo and A. G. Cudworth, "Can Future Type 1 Diabetes be Predicted. A Study in Families of Affected Children", *Diabetes*, 31, 862-866, (1982)). In contrast, the highest population-based absolute risk for IDDM, i.e., that for an individual with both HLA-DR3 and DR4, is only 2-4% (P. Platz, B. K. Jakobsen, N. Morling, L. P. Ryder, A. Svejgaard, J. Thomsen, M. Christy, H. Kromann, J. Benn, J. Nerup, A. Green and M. Hauge, "HLA-D and -DR Antigens in Genetic Analysis of Insulin Dependent Diabetis Mellitus", *Diabetologia*, 21, 108-115, (1981)); C. Johnston, D. A. Pyke, A. G. Cudworth and E. Wolf, "HLA-DR Typing in Identical Twins with Insulin-Dependent Diabetes: Difference Between Concordant and Discordant Pairs", *Br. Med. J.*, 286, 253-255, (1983); J. I. Rotter, C. M. Vadheim, L. J. Raffel and D. L. Rimoin, "Genetics, Diabetes Mellitus Heterogeneity, and Coronary Heart Disease", D. C. Rao, R. E. Elston, L. H. Kuller, M. Feinlieb, C. Carter and R. Havlik (eds.): *The Genetic Epidemiology of Coronary Heart Disease*, Alan R. Liss; New York, (1984)). The absolute risks for the remaining predisposing genotypes are considerably lower. If the susceptibility to IDDM is due solely to these DR genes, as currently characterized, then the absolute risk should be similar for family members and persons with identical HLA genotypes in the population. Clearly they are not. This significant difference between the population and family data strongly suggests that HLA-DR3 and DR4, as currently serologically defined, do not themselves cause susceptibility to IDDM and that further work is needed to find markers which truly correlate with the development of IDDM.

According to current knowledge, the HLA-D region consists of at least 13 loci: three DR, two Q, two DP beta genes, and one DZ, one DR, two DQ and two DP alpha genes (F.H. Bach, "The HLA Class II Gene Products: The HLA-D Region", *Immunology Today*, 6, 89–96, (1985)). D. Owerbach, A. Lernmark, P. Platz, P. Pyder, L. Rask, P. A. Peterson and J. Ludsigsson, "HLA-DR Beta-chain DNA Endonuclease Fragments Differ Between Healthy and Insulin-Dependent Diabetic Individuals", *Nature*, 303, 815-817, (1983); Haguenauer et al, *PNAS*, Vol. 82, pp. 3335-3339, (1985); and Arnheim et al, *PNAS*, Vol. 82, pp. 6970-6974, (1985) have investigated polymorphisms of the HLA-D region using a HLA-DQ beta cDNA probe on DNA from lymphocytes isolated from IDDM patients and controls and report an increased frequence of certain restriction fragments in controls versus HLA-DR matched IDDM patients. While those methods increase the strength of association of HLA markers and IDDM compared with serologic tests, the association is still not specific enough to determine with a high degree of accuracy proclivity in human individuals to develop IDDM.

PCT WO 83/03260 concerns a method for determining tissue types coded by MHC genes.

Canadian Patent 1,186,991 concerns a method for the determination of liability in humans to develop non-insulin-dependent diabetes mellitus (NIDDM).

SUMMARY OF THE INVENTION

An object of the present invention is to provide specific probes for the determination of proclivity in human individuals to develop autoimmune disease, such as, IDDM by detecting disease susceptibility sequences or sequences linked thereto in human DNA.

The above object and other objects and advantages are fulfilled by the present invention.

The present invention concerns the following probes:

(1) an oligonucleotide (intervening sequence probe, i.e., prepared from intervening sequences located between Exons 3 and 4 of λ DR 5.0 and λ DR 4.0) comprising one of the following core sequences of nucleic acids:

(a) from λ DR 4.0:

GTACCCCCTGGGGAAGCAGTCATGCCTGCCAAGCAGG

AGAGGCTGTCCCTCTTTTGAACCTCCCCATGATGTCAC

AAGTCGGGGTCACCTGCTGTCTGTGGGCTCCAGGCCC

TGCCTCTGGGACAGAGACTGAGTTTCTGGTAC;

(b) from λ DR 5.0:

TCTAGAAACACCTGTACCTCCTGGAGAAGCAGTCTCG

CCTGCCAAGCAGGAGAGGCTGTCCCTCTTTTGAACCT

CCCCATGATGTCACAGGTCAGGGTCACCCTCCCTCCCC

-continued

GGGCTCCAGGCACTGCCTCTGGGTCTGAGACTGAGTT

TCTGGTGCTGTTGATCTGAGTTATTTGTTGTGATCTGG

GAAGAGGAGAAGTGTAGGGACCTTCCTGACATGAGG

GGAGTCCAATCTCAGCTCTGCCTTTTATTAGCTCTGTC

ACTCTAGA, the oligonucleotides not exceeding 10 kb, and complementary sequences (reverse complements) thereto.

(2) Nucleotide sequences of Exon 2 of two DQ beta and 3DR beta genes, namely, (a) a λ HLA-DQ-4 nucleic acid sequence comprising no more than 50 base pairs, the sequence containing a 17 or 19 nucleic acid core sequence selected from the group consisting of

GAGAGGAGTACGCACGCTT,

GGCCGCCTGCCGCCGAG, and

AGGACCCGGGCGGAGTTGG, and complementary sequences thereto;

(b) a λ HLA-DQ-3 nucleic acid sequence containing no more than 50 base pairs, the sequence comprising a 17 or 19 nucleic acid core sequence selected from the group consisting of

GAGAAGAGATCGTGCGCTT,

GCTGGGGCTGCCTGCCG, and

AGGAAACGGGCGGCGGTGG, and complementary sequences thereto;

(c) a λ HLA-DR-5.0 nucleic acid sequence containing no more than 50 base pairs, the sequence comprising a 19 nucleic acid core sequence selected from the group consisting of

GGAGCAGGTTAAACATGAG,

ATACTTCTATCACCAAGAG,

GGAGCAGAAGCGGGCCGCG and

CGGGGTTGGTGAGAGCTTC, and complementary sequences thereto;

(d) a λ HLA-DR-4.0 nucleic acid sequence containing no more than 50 base pairs, the sequence comprising a 19 nucleic acid core sequence selected from the group consisting of

GGAGTACTCTACGTCTGAG,

ATACTTCCATAACCAGGAG, and

GGAGCAGAAGCGGGGCCGG, and complementary sequences thereto;

(e) a λ HLA-DR-4.3 nucleic acid sequence containing no more than 50 base pairs, the sequence comprising a 19 nucleic acid core sequence selected from the group consisting of

GGAGCAGGCTAAGTGTGAG,

ATACATCTATAACCAAGAG, and

GGAGCGGAGGCGGGCCGAG, and complementary sequences thereto.

(3) probes derived from of a HLA-DQ beta gene:

(a) Exon 2 and flanking regions on both sides thereof, each of the flanking regions being no greater than 5 kb, particularly a 1.3 kb Hind III fragment, and (b) the region downstream of Exon 5, (to the right of Exon 5- see FIG. 8) the fragment being not greater than 10 kb, particularly a 2.0 kb Taq fragment.

The present invention also concerns a method for detecting the proclivity in a human for development of an autoimmune disease, e.g., insulindependent diabetes millitus, the method comprising (a) isolating DNA isolated from peripheral blood lymphocytes, (b) treating the DNA isolated from step (a) with a restriction enzyme to yield DNA-fragments, (c) separating the DNA-fragments from step (b) into fragments of different molecular masses, e.g., by using gel electrophoresis, (d) transferring the separated DNA-fragments with a (c) to a filter which binds the DNA, (e) contacting the bound DNA from step (a) with (i) a labeled oligonucleotide having a nucleic acid core sequence. selected from the group consisting of

| | |
|---|---|
| GTACCCCTGGGGAAGCAGTCATGCCTGCCAAGC | (1) |
| AGGAGAGGCTGTCCCTCTTTTGAACCTCCCCATGATGT | |
| CACAAGTCGGGGTCACCTGCTGTCTGTGGGCTCCAGG | |
| CCCTGCCTCTGGGACAGAGACTGAGTTTCTGGTAC, | |
| TCTAGAAACACCTGTACCTCCTGGAGAAGCAGTC | (2) |
| TCGCCTGCCAAGCAGGAGAGGCTGTCCCTCTTTTGAA | |
| CCTCCCCATGATGTCACAGGTCAGGGTCACCCTCCCTC | |
| CCCGGGCTCCAGGCACTGCCTCTGGGTCTGAGACTGA | |
| GTTTCTGGTGCTGTTGATCTGAGTTATTTGTTGTGATC | |
| TGGGAAGAGGAGAAGTGTAGGGACCTTCCTGACATG | |
| AGGGGAGTCCAATCTCAGCTCTGCCTTTTATTAGCTCT | |
| GTCACTCTAGA, | |
| GAGAGGAGTACGCACGCTT, | (3) |
| GGCCGCCTGCCGCCGAG, | (4) |
| AGGACCCGGGCGGAGTTGG, | (5) |
| GAGAAGAGATCGTGCGCTT, | (6) |
| GCTGGGGCTGCCTGCCG, | (7) |
| AGGAAACGGGCGGCGGTGG, | (8) |
| GGAGCAGGTTAAACATGAG, | (9) |
| ATACTTCTATCACCAAGAG, | (10) |
| GGAGCAGAAGCGGGCCGCG | (11) |
| CGGGGTTGGTGAGAGCTTC, | (12) |
| GGAGTACTCTACGTCTGAG, | (13) |

| -continued | | | -continued | |
|---|---|---|---|---|
| ATACTTCCATAACCAGGAG, | (14) | | GAGAAGAGATCGTGCGCTT, | (6) |
| GGAGCAGAAGCGGGGCCGG, | (15) | | GCTGGGGCTGCCTGCCG, | (7) |
| GGAGCAGGCTAAGTGTGAG, | (16) | | AGGAAACGGGCGGCGGTGG, | (8) |
| ATACATCTATAACCAAGAG, | (17) | | GGAGCAGGTTAAACATGAG, | (9) |
| GGAGCGGAGGCGGGCCGAG, | (18) | | ATACTTCTATCACCAAGAG, | (10) |
| CGTGCGTCTTGTGACCAGA | (19) | | GGAGCAGAAGCGGGCCGCG | (11) |
| | | | CGGGGTTGGTGAGAGCTTC, | (12) |
| | | | GGAGTACTCTACGTCTGAG, | (13) |
| | | | ATACTTCCATAACCAGGAG, | (14) |
| | | | GGAGCAGAAGCGGGGCCGG, | (15) |
| | | | GGAGCAGGCTAAGTGTGAG, | (16) |
| | | | ATACATCTATAACCAAGAG, | (17) |
| | | | GGAGCGGAGGCGGGCCGAG, | (18) |
| | | | CGTGCGTCTTGTGACCAGA | (19) | and complementary sequences thereto, sequences (1) and (2) not exceeding 10 kb sequences, sequences (3) to (19) not exceeding 50 base pairs, or with (ii) a labeled DQ beta gene fragment of HLA including Exon 2 and flanking regions on both sides thereof each of the flanking regions being no greater than 5 kb, or with (iii) a labeled DQ beta gene fragment of HLA disposed downstream of Exon 5, (f) washing the filters and (g) determining the degree of binding between the bound DNA and the labeled nucleic acid sequence or labeled gene fragment.

In the above described method, the nucleic acid sequence is preferably radioactive labeled and the binding is detected by autoradiography.

The present invention further concerns a method for detecting the proclivity in a human for development of an HLA association disease, the method comprising (a) contacting a sample containing DNA isolated from human blood lymphocytes, (b) treating the DNA isolated from step (a) with a restriction enzyme to yield DNA-fragments, (c) separating the DNA-fragments from step (b) into fragments of different molecular masses, (d) transferring the separated DNA-fragments from step (c) to a filter which binds the DNA, (e) contacting the bound DNA from step (a) with (i) a labeled oligonucleotide having a nucleic acid core sequence selected from the group consisting of

| | |
|---|---|
| GTACCCCCTGGGGAAGCAGTCATGCCTGCCAAGC | (1) |
| AGGAGAGGCTGTCCCTCTTTTGAACCTCCCCATGATGT | |
| CACAAGTCGGGGTCACCTGCTGTCTGTGGGCTCCAGG | |
| CCCTGCCTCTGGGACAGAGACTGAGTTTCTGGTAC, | |
| TCTAGAAACACCTGTACCTCCTGGAGAAGCAGTC | (2) |
| TCGCCTGCCAAGCAGGAGAGGCTGTCCCTCTTTTGAA | |
| CCTCCCCATGATGTCACAGGTCAGGGTCACCCTCCCTC | |
| CCCGGGCTCCAGGCACTGCCTCTGGGTCTGAGACTGA | |
| GTTTCTGGTGCTGTTGATCTGAGTTATTTGTTGTGATC | |
| TGGGAAGAGGAGAAGTGTAGGGACCTTCCTGACATG | |
| AGGGGAGTCCAATCTCAGCTCTGCCTTTTATTAGCTCT | |
| GTCACTCTAGA, | |
| GAGAGGAGTACGCACGCTT, | (3) |
| GGCCGCCTGCCGCCGAG, | (4) |
| AGGACCCGGGCGGAGTTGG, | (5) | and complementary sequences thereof, sequences (1) and (2) not exceeding 10 kb, sequences (3) to (19) not exceeding 50 base pairs, or with (ii) a labeled DQ beta gene fragment of HLA including Exon 2 and flanking regions on both sides thereof, each of the flanking regions being no greater than 5 kb, or with (iii) a labeled DQ beta gene fragment of HLA disposed downstream of Exon 5, the fragment being not greater than 10 kb, (f) washing the filters and (g) determining the degree of binding between the bound DNA and the labelled nucleic acid sequence or labeled gene fragment.

and determining the binding between the sample and the labeled oligonucleotide or fragment.

The present invention is also directed to an oligonucleotide of 10 to 50 base pairs that differentiates nucleotide sequences coding for amino acid residues 26, 37, 38 and/or 57 of the HLA-DQ beta gene. Preferably such amino acid residues are selected from the group consisting of $^{26}$Gly, $^{26}$Tyr, $^{37}$Ile, $^{38}$Val and $^{57}$Ala.

The present invention can be employed with PCR (polymerase chain reaction) metholology (Saiki et al, Nature, 324, 163–166, (1986)), i.e., DNA amplified using PCR and used with oligonucleotide probes of the invention to detect genes at high risk for diabetes or another autoimmune disease.

| DEFINITIONS | |
|---|---|
| Amino Acid Code Words (as appearing in FIG. 3) | |
| Asp | aspartic acid |
| Asn | asparagine |
| Thr | threonine |
| Ser | serine |
| Glu | glutamic acid |
| Gln | glutamine |
| Pro | proline |
| Gly | glycine |
| Ala | alanine |
| Cys | cysteine |
| Val | valine |
| Met | methionine |
| Ile | isoleucine |
| Leu | leucine |
| Tyr | tyrosine |
| Phe | phenylalanine |

| -continued | |
| --- | --- |
| DEFINITIONS | |
| Trp | tryptophane |
| Lys | lysine |
| His | histidine |
| Arg | arginine |
| Nucleic Acid Code Words (as appearing in FIG. 2) | |
| A | adenine |
| G | guanine |
| C | cytosine |
| T | thymidine |
| U | uracil |
| HLA | human leucocyte antigen (histocompatibility antigen) |
| core sequence: | containing at least the specific 19 nucleic acid sequence, but may include additional nucleic acids on one or both sides thereof. |

BRIEF DESCRIPTION OF THE DRAWINGS

FIG. 1 is a restriction map of three DR beta genes isolated from an IDDM patient.

FIG. 2 comprised of FIGS. 2a and 2b are nucleotide sequences of λ DR 5.0, λ DR 4.3 and λ DR 4.0.

FIG. 2a: The complete sequence of exon 2 from λ DR 5.0, is shown, while only differences in this sequence are indicated in λ DR 4.3 and λ DR 4.0.

FIG. 2b: The complete sequence of Hind III-Bam HI fragment indicated in FIG. 1 is shown for λ DR 5.0 (1-1882). Differences to this sequence are indicated for λ DR 4.3 and λ DR 4.0, but only in the exon regions.

Figure 3A:
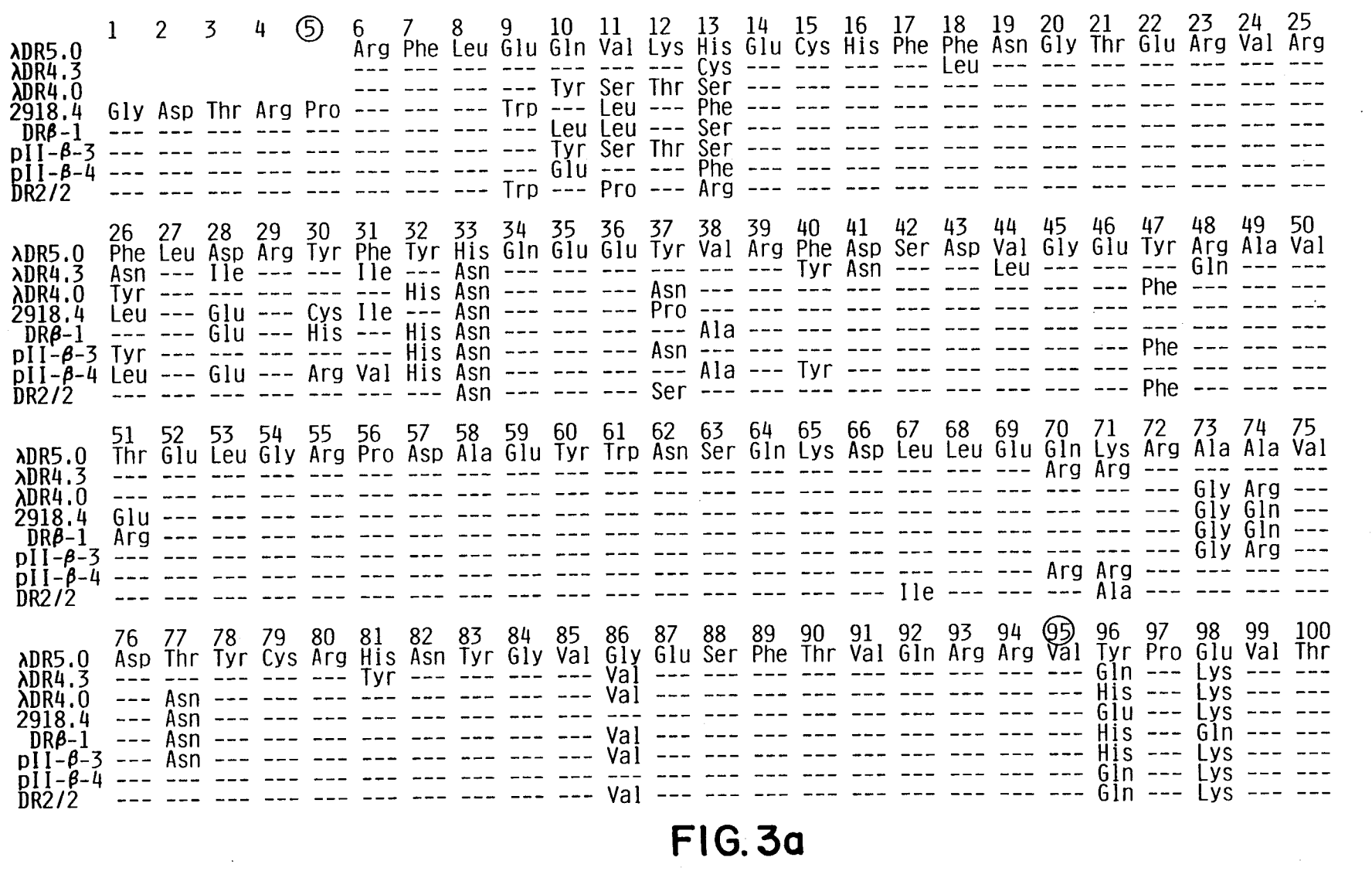

FIGS. comprised of FIGS. 3a, 3b and 3c shows predicted amino acid sequences from λ DR 5.0, λ DR 4.3 and λ DR 4.0.

FIG. 4 shows the sequences of two probes prepared from intervening sequences located between Exons 3 and 4 of λ DR 5.0 (Probe A) and λ DR 4.0 (Probe B), respectively (see FIG. 1).

Figure 5A:
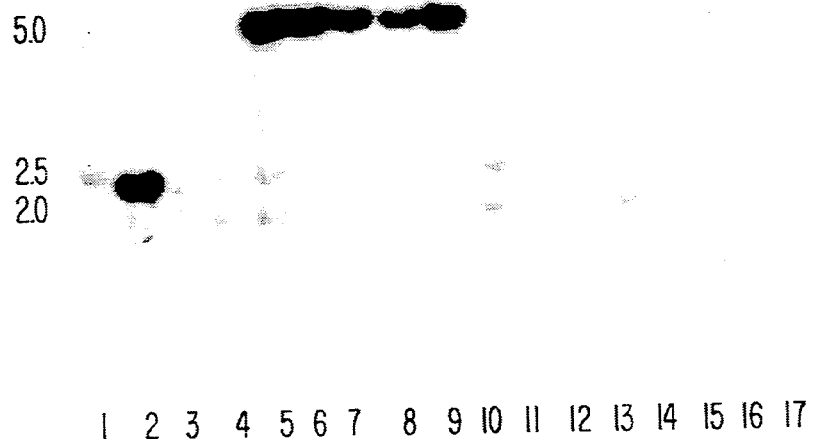
Figure 5B:
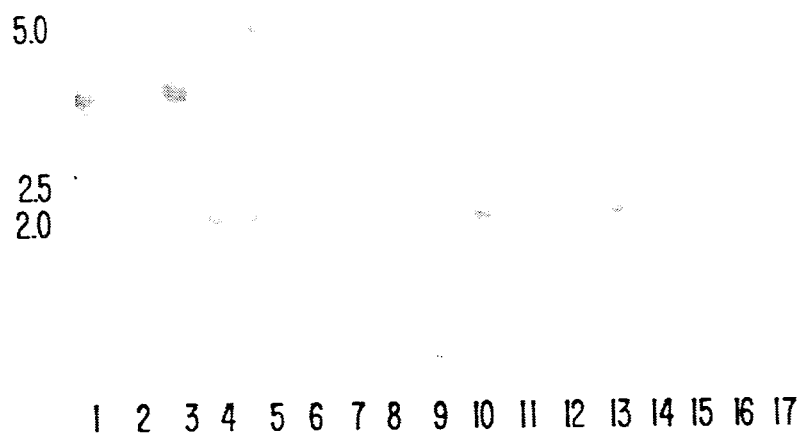

FIG. 5 comprised of FIGS. 5A and 5B shows a Southern blot hybridization using the λ DR 5.0 and λ DR 4.0 intervening sequence probes.

Figure 6:
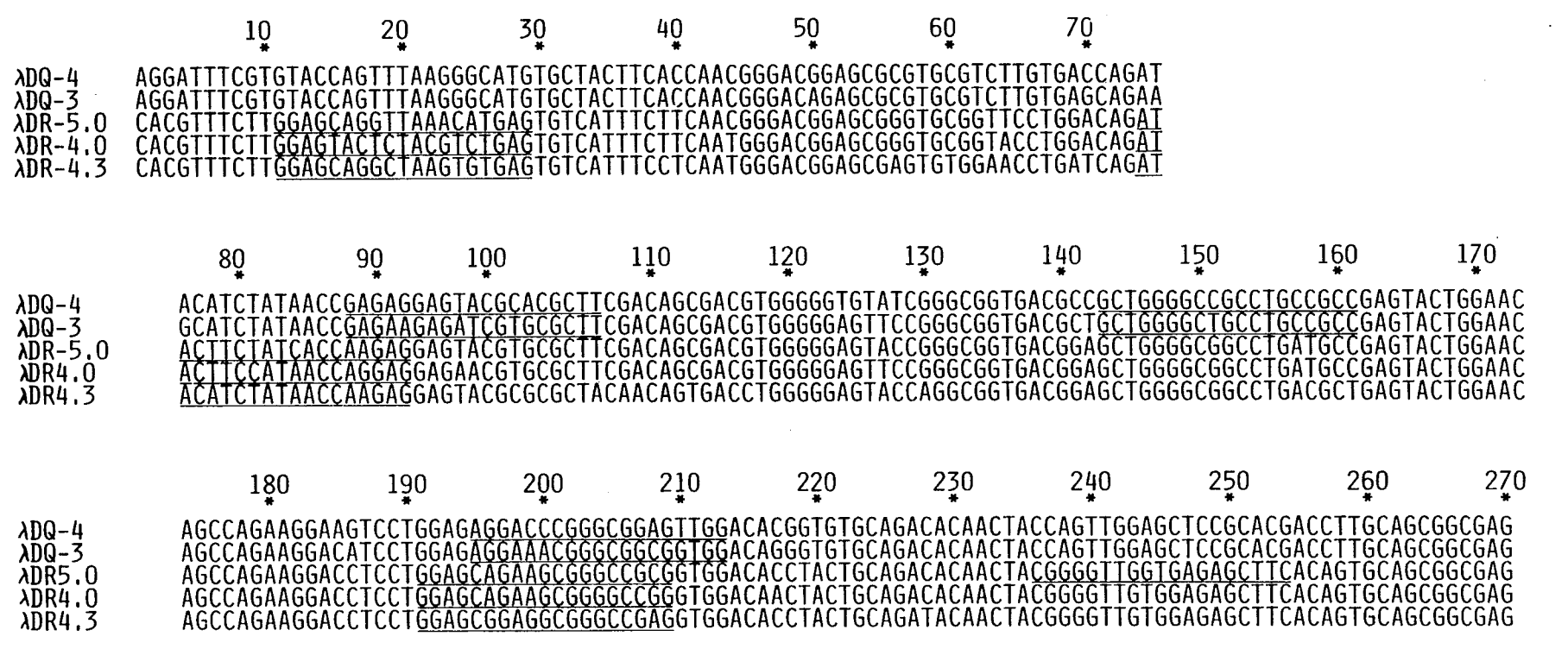

FIG. 6 shows the nucleotide sequence of exon 2 (coding for the amino terminal domain) of two DQβ and three DRβ genes isolated from an IDDM patient.

FIG. 7 shows the construct and use of two oligonucleotide probes prepared from exon 2 in a dot blot assay.

Figure 8:
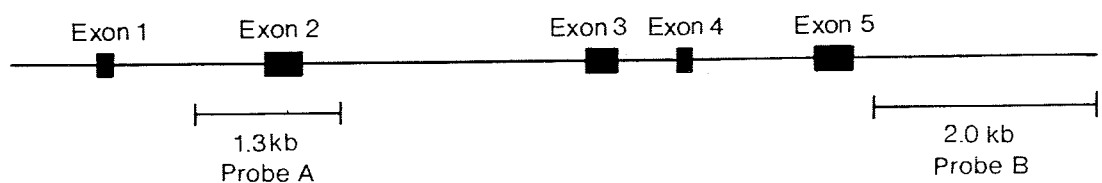

FIG. 8 shows the regions of a HLA-DQβ gene isolated from a IDDM patient and used to derive two DQβ specific DNA probes.

Figure 9A:
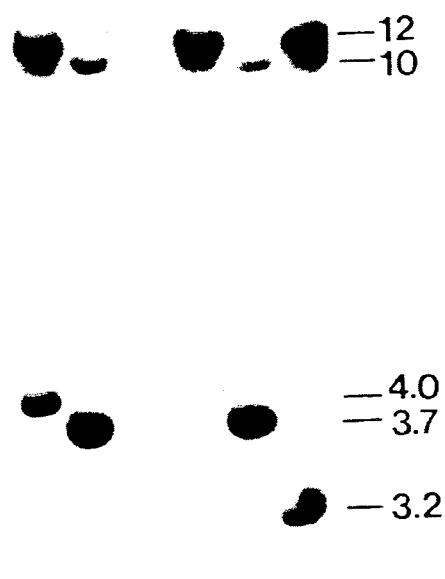
Figure 9B:
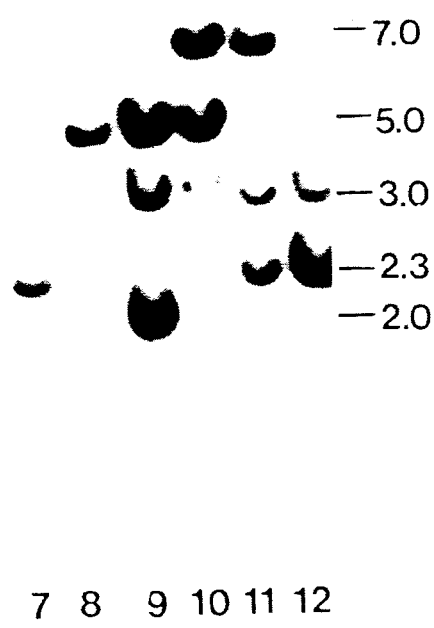

FIGS. 9 comprised of FIGS. 9A and 9B shows the use of the DQβ specific probes with blot hybridization.

DETAILED DESCRIPTION OF THE INVENTION

The present invention concerns nucleic acid sequences derived from the HLA-D region that can be employed to detect the proclivity of an individual to develop autoimmune diseases such as insulin-dependent diabetes, ankylosing spondylitis, Reiter's disease, systemic lupus crythematosus, Sjorgen's syndrome, myasthenia gravis, acute anterior ureitis, rheumatoid arthritis, multiple sclerosis, celiac disease, dermatitis herpetiformis, chronic autoimmune hepatitis, sicca syndrome, idiopathic Addison's disease, subacute thyroiditis, psoriaris vulgaris, idiopathic hemachromatosis, C2 deficiency, congenital adrenal hyperplasia and Grave's disease, just to name a few. The present invention is particularly directed to detecting the proclivity of a human for developing insulin-dependent diabetes mellitus.

The probes of the present invention can also be utilized in tissue typing (typing by lymphocytotoxicity) and for determination of paternity.

The probes of the present invention have a high degree of specificity thereby restriction fragments, even of identical size, can be differentiated through differential amounts of binding of probe (hybridization).

The probes of the present invention generally fall into one of the following three categories:

(i) intervening sequences or sequences flanking the HLA-D region genes, (ii) oligonucleotide probes prepared from polymorphic regions of the HLA-D region which, encode, mRNA, and (iii) DNA sequences of human genomic DNA located within the HLA-D region of $20 \times 10^6$ base pairs from the ends of the region.

In a preferred embodiment of the invention, purified genomic DNA fragments containing intervening sequences or oligonucleotide sequences of 10–50 base pairs are radioactively labelled. The labelled preparations are used to probe human DNA by the Southern hybridization technique. In short, DNA isolated from peripheral blood lymphocytes is treated with restriction enzymes to yield DNA-fragments of variable sizes. The DNA-fragments are separated into fragments of different molecular masses by gel electrophoresis and transferred to filters which bind the DNA. After exposure to the labelled DNA probe, which will bind only to (hybridize) DNA-fragments containing related nucleotide sequences, binding of the radioactive probe to DNA fragments is identified by autoradiography (see *Genetic Engineering*, 1, ed. Robert Williamson, Academic Press, (1981), 72–81). Alternatively, human DNA is bound directly to filters to which the radioactive probe binds specific sequences and the degree of binding is quantitated by directly counting the radioactive emissions.

The probes of the present invention can be used for examining the distribution of the specific fragments detected, as well as the quantitative (relative) degree of binding of the probe, for determining the occurrence of specific strongly binding (hybridizing) sequences, thus indicating a liability for an individual to be at low risk or high risk for developing an autoimmune disease, such as, IDDM.

For the most part, the probe will be labeled with an atom or inorganic radical, most commonly using radionuclides, but also perhaps heavy metals.

Conveniently, a radioactive label may be employed. Radioactive labels include $^{32}P$, $^{3}H$, $^{14}C$, or the like. Any radioactive label may be employed which provides for an adequate signal and has sufficient half-life. Other labels include ligands, which can serve as a specific binding member to a labeled antibody, fluorescers, chemiluminescers, enzymes, antibodies which can serve as a specific binding pair member for a labeled ligand, and the like. A wide variety of labels have been employed in immunoassays which can readily be employed in the present assay. The choice of the label will be governed by the effect of the label on the rate of hybridization and binding of the probe to the genetic DNA. It will be necessary that the label provide sufficient sensitivity to detect the amount of DNA available for hybridization. Other considerations will be ease of synthesis of the probe, readily available instrumentation, ability to automate, convenience, and the like.

The manner in which the label is bound to the probe will vary depending upon the nature of the label. For a radioactive label, a wide variety of techniques can be employed. Commonly employed is nick translation with an α-$^{32}$P-dNTP or terminal phosphate hydrolysis with alkaline phosphatase followed by labeling with radioactive $^{32}$P employing γ-$^{32}$P-NTP and T4 polynucleotide kinase. Alternatively, nucleotides can be synthesized where one or more of the elements present are replaced with a radioactive isotope, e.g., hydrogen with tritium. If desired, complementary labeled strands can be used as probes to enhance the concentration of hybridized label.

Where other radionuclide labels are involved, various linking groups can be employed. A terminal hydroxyl can be esterified, with inorganic acids, e.g,. $^{32}$P phosphate, or $^{14}$C organic acids, or else esterified to provide linking groups to the label. Alternatively, intermediate bases may be substituted with activatable linking groups which can then be linked to a label.

Ligands and antiligands may be varied widely. Where a ligand has a natural receptor, namely ligands such as biotin, thyroxine, and cortisol, these ligands can be used in conjunction with labeled naturally occurring receptors. Alternatively, any compound can be used, either haptenic or antigenic, in combination with an antibody.

Enzymes of interest as labels will primarily be hydrolases, particularly esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol.

The probe is employed for hybridizing to a gene affixed to a water insoluble porous support. The single stranded nucleic acid is affixed. Depending upon the source of the nucleic acid, the manner in which the nucleic acid is affixed to the support may vary.

The clinical isolate or specimen is spotted or spread onto a filter to provide a plurality of individual portions. The filter is an inert porous solid support, e.g., nitrocellulose. The clinical isolate is blood. Conveniently, a microfilter is employed, which inhibits the passage of the cells through the filter.

The cells are then treated to liberate their DNA. Lysis conditions are devised such that the cells do not migrate and their DNA remains affixed in place on the surface where they were situated. The lysing and DNA denaturing, as well as the subsequent washings, can be achieved by placing the filter containing the cells isolate side up, onto a bibulous support saturated with an appropriate solution for a sufficient time to lyse the cells and denature the DNA. For lysing, chemical lysing will conveniently be employed, usually dilute aqueous alkali, e.g., 0.1 to 1M NaOH. The alkali will also serve to denature the DNA. Other denaturation agents include, elevated temperatures, organic reagents, e.g., alcohols, amides, amines, ureas, phenols and sulfoxides or certain inorganic ions, e.g., thiocyanate and perchlorate.

After denaturation, the filter is washed in an aqueous buffered solution, generally at a pH of about 6 to 8, usually 7. Of the many different buffers that may be used, tris is an example. One or more washings may be involved, conveniently using the same procedure as employed for the lysing and denaturation.

After the lysing, denaturing and washes have been accomplished, the DNA spotted filter is dried at an elevated temperature, generally from about 50° to 70° C. The DNA is now fixed in position and can be assayed with the probe when convenient. This fixing of the DNA for later processing has great value for the use of this technique in filed studies, remote from laboratory facilities.

Hybridization may now be accomplished. The filter is incubated at a mildly elevated temperature for a sufficient time with the hybridization solution without the probe to thoroughly wet the filter. Various hybridization solutions may be employed, comprising from about 20 to 60 volume, preferably 30, percent of an inert polar organic solvent. A common hybridization solution employs about 50% formamide, about 0.5 to 1M sodium chloride, about 0.05 to 0.1M sodium citrate, about 0.05 to 0.2% sodium dodecylsulfate, and minor amounts of EDTA, ficoll (about 300-500 kdaltons), polyvinylpyrrolidone, (about 250-500 kdaltons) and serum albumin. Also included in the hybridization solution will generally be from about 0.5 to 5 mg/ml of sonicated denature DNA, e.g., calf thymus of salmon sperm; and optionally from about 0.5 to 2% wt/vol glycine. Other additives may also be included, such as dextran sulfate of from about 100 to 1,000 kdaltons and in an amount of from about 8 to 15 weight percent of the hybridization solution.

The particular hybridization technique is not essential to the invention. Other hybridization techniques are described by Gall and Pardue (1969) *Proc. Natl. Acad. Sci,* 63, 378-383 and John, Burnsteil and Jones, *Nature,* 223, 582-587, (1969). As improvements are made in hybridization techniques they can readily be applied.

The amount of labeled probe which is present in the hybridization solution will vary widely, depending upon the nature of the label, the amount of the labeled probe which can reasonably bind to the filter, and the stringency of the hybridization. Generally, substantial excesses over stoichiometric of the probe will be employed to enhance the rate of binding of the probe to the fixed DNA.

Various degrees of stringency of hybridization will be employed. The more severe the conditions, the greater the complementarity that is required for hybridization between the probe and the ssDNA for duplex formation. Severity can be controlled by temperature, probe concentration, probe length, ionic strength, time, and the like. Conveniently, the stringency of hybridization is varied by changing the polarity of the reactant solution by manipulating the concentration of formamide in the range of 20% to 50%. Temperatures employed will normally be in the range of about 20° to 80° C., usually 30° to 75° C.

After the filter has been contacted with a hybridization solution at a moderate temperature for an extended period of time, the filter is then introduced into a second solution having analogous concentrations of sodium chloride, sodium citrate and sodium dodecylsulfate as provided in the hybridization solution. The time for which the filter is maintained in the second solution may vary from five minutes to three hours or more. The second solution determines the stringency, dissolving cross duplexes and short complementary sequences. After rinsing the filter at room temperature with dilute sodium citrate-sodium chloride solution, the filter may now be assayed for the presence of duplexes in accordance with the nature of the label. Where the label is radioactive, the filter is dried and exposed to X-ray film.

The invention is further described by reference to the following non-limiting examples.

EXAMPLES

EXAMPLE 1

Isolation of HLA-DR Beta Genes

A chromosomal gene library was prepared from an HLA-DR3/4 IDDM patient which were previously analyzed with an HLA-DQβcDNA probe (Owerbach et al, 1983, supra). The patient had the following HLA-A, B, C and DR types: A2 28; B7, 40, C3; DR 3,4. Five hundred thousand recombinant λ phases were screened with an HLA-DR beta-chain cDNA probe (Owerbach, 1983, supra). A large molecular DNA mass from the patient was partially cleaved with the restriction endonuclease Sau3A, and 10–20 kb sequences were isolated by fractionation on a 10–40% sucrose gradient. This size-selected DNA was ligated with bacteriophage lambda L47 DNA cleaved with Bam HI, and the resulting mixture was packaged using in vitro packaging extracts (Amersham, Arlington Heights, Ill.). Approximately $1-2 \times 10^6$ recombinant phage were amplified to prepare a library according to the method of T. Maniatis, E. F. Fritsh and J. Sambrook, J. eds., *Molecular Cloning, A Laboratory Manual*, pp. 293–294, Cold Spring Harbor Laboratory, New York, (1982). Five hundred thousand recombinant phage were screened with an HLA-DQβ- chain cDNA probe (D. Larhammar, L. Schenning, K. Gustafsson, K. Wiman, L. Claesson, L. Rask and P. A. Peterson, "Complete Amino Acid Sequence of an HLA-DR Antigen-Like β Chains Predicted from the Nucleoside Sequence: Similarities With Immunoglobulins and HLA-A, -B and -C Antigens", *Proc. Natl. Acad. Sci. USA*, 79, 3687–3691, (1982)). Conditions were used that allowed cross-hybridization with DRβ sequences. Three positive clones, λDR 5.0, λDR 4.3 and λDR. 4.0 were isolated and further characterized. After Bam HI digestion, the clones were subcloned via Bam HI-digested BAP-treated pUC-13 (P-L Biochemicals, Milwaukee, Wis.) and mapped using standard restriction mapping procedures (Maniatis et al, 1982, supra).

The restriction endonuclease maps of the 5.0, 4.0 and 4.3 kb Bam HI fragments of three genes DR 5.0, 4.0 and 4.3 respectively, are shown in FIG. 1. The boxed areas are exons (areas which code for mRNA found in the cytoplasm of cells).

Figure 2A:
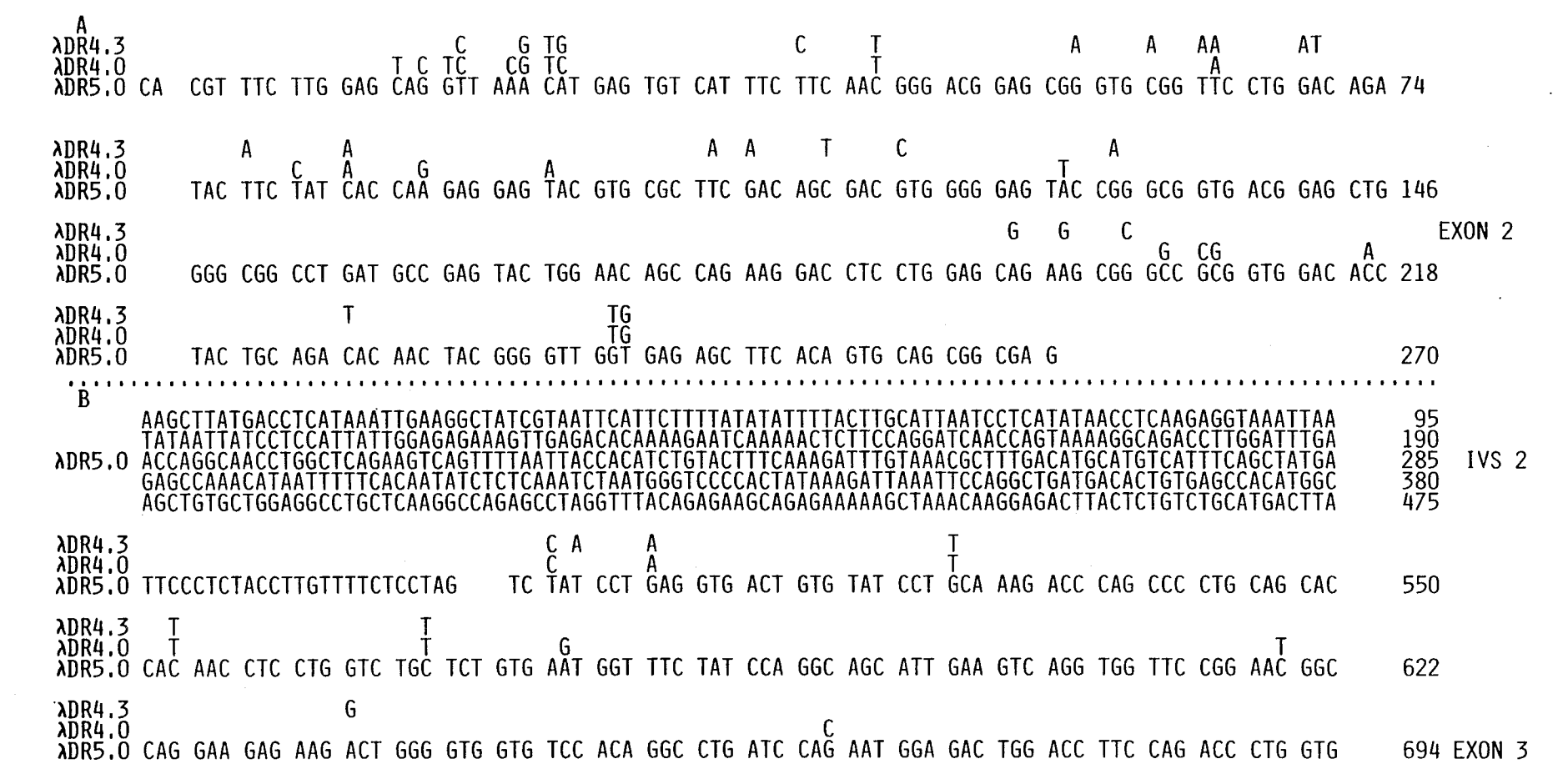
Figure 2B:
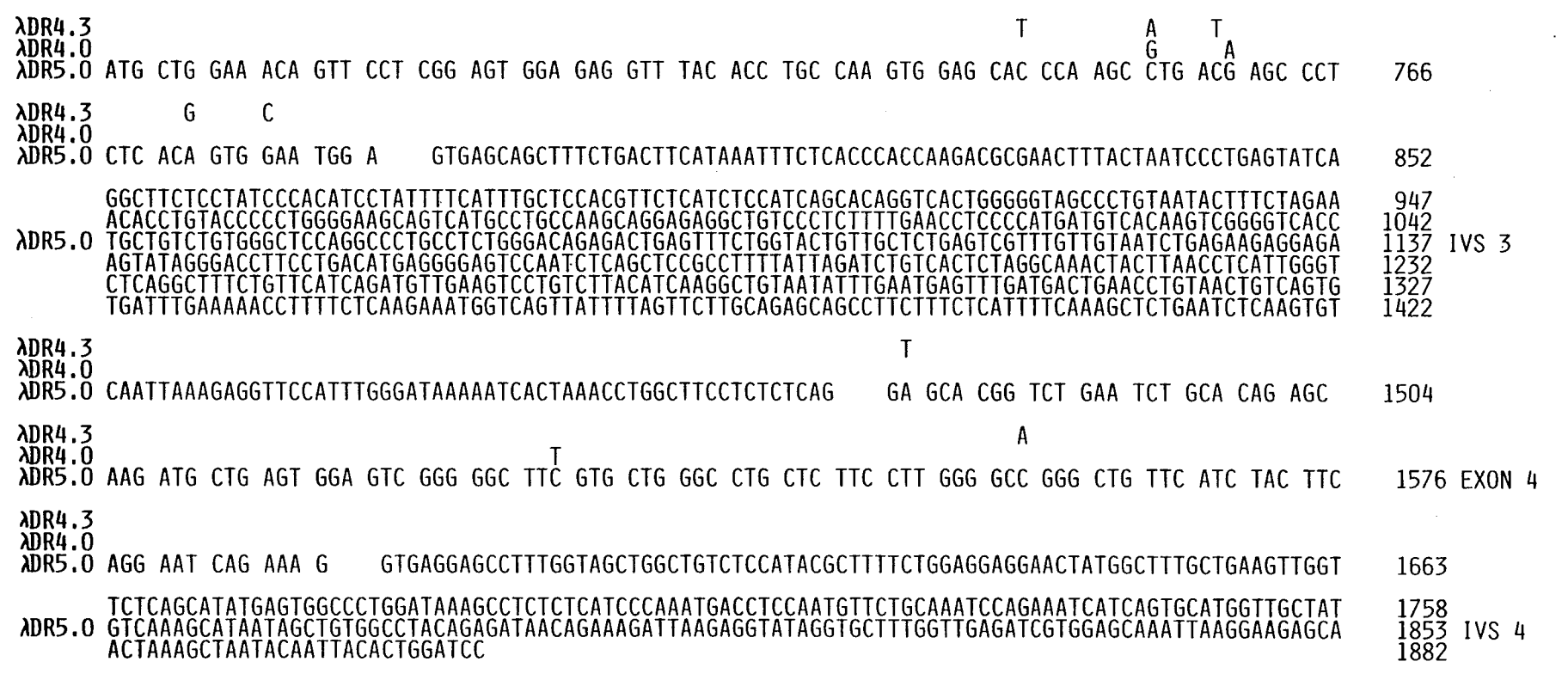

While restriction endonuclease sites are similar λDR 4.0 and λDR 4.3, those of λDR 5.0 are quite different, especially in the intervening sequence region separating exons 2 and 3. The identification and localization of the exon regions were determined by nucleotide sequence analysis (FIG. 2). This analysis reveals that the three genes contain exon 2, 3, and 4 sequences: the second and third exons encode the two extracellular domains, β1 and β2, respectively, while the fourth exon encodes the connecting peptide, the membrane-spanning segment, and six amino acids of the cytoplasmic tail (D. Larhammar, L. Schenning, K. Gustafsson, K. Wiman, L. Claesson, L. Rask and P. A. Peterson, "Complete Amino Acid Sequence of an HLA-DR Antigen-like β Chain as Predicted from the Nucleotide Sequence: Similarities With Immunoglobulins and HLA-A, -B and -C antigens, *Proc. Natl. Acad. Sci., USA*, 79, 3687–3691, (1982); E. O. Long, C. T. Wake, E. Gorski and B. Mach, "Complete Sequence of an HLA-DR β Chain Deduced from a cDNA Clone and Identification of Multiple Non-allelic DR β Chain Genes", *EMBO J.*, 2, 389–394, (1983)). Moreover, the exon sequences are highly homologous (~90%) to published DRβ sequences (Long et al, 1983, supra; K. Gustafsson, L, Wiman, E. Emmoth, D. Larhammar, J. Bohme, J. J. Hyldig-Nielsen, H. Ronne, P. A. Peterson and L. Rask, "Mutations and Selection in the Generation of Class II Histocompatibility Antigen Polymorphism", *EMBO J.*, 3, 1655–1661, (1984); J. I. Bell, P. Estess, T. S. John, R. Saiki, D. C. Watling, H. A. Erlich and H. O. McDevitt, "DNA Sequence and Characterization of Human Class II Major Histocompatibility Complex β Chains from the DR1 Haplotype", *Proc. Natl. Acad. Sci. USA*, 82, 3405–3409, (1985)), whereas they have a much weaker homology to DQB (Larhammar et al, 1982, supra; P. Larhammar, J. J. Hyldig-Nielsen, B. Servenius, G. Andersson, L. Rask and P. A. Peterson, "Exon-intron Organization and Complete Nucleotide Sequence of a Human Major Histocompatibility Antigen DCβ gene", *Proc. Natl. Acad. Sci. USA*, 80, 7313–7317, (1983); L. Schenning, D. Larhammar, P. Bill, K. Wiman, A. K. Jonsson, L. Rask and P. A. Peterson, "Both the A and β Chains of HCL-DC Class II Histocompatibility Antigens Display Extensive Polymorphism in their Aminoterminal Domains", *EMBO J.*, 3, 447–452, (1984); J. M. Boss and J. L. Strominger, "Cloning and Sequence Analysis of the Human Major Histocompatibility Complex Gene DC-3β", *Proc. Natl. Acad. Sci. USA*, 81, 5199–5203, (1984)) and DPB sequences, (K. Gustafsson, E. Emmoth, E. Widmark, J. Bohme, P. A. Peterson and L. Rask, "Isolation of a cDNA Clone Coding for an SB β-chain", *Nature*, 309, 76–78, (1984); A. Kelly and J. Trowsdale, "Complete Nucleotide Sequence of a Functional HLA-DPβ Gene and the Region Between the DPβ1 and DPα1 genes: Comparison of the 5' Ends of HLA Class II Genes", *Nucleic Acid Res.*, 13, 1608–1621, (1985)).

The DRB-gene sequences of λDR 5.0, 4.0 and 4.3 are very different to those of a previously published DRβ pseudogene isolated from a homozygous DR4/4 individual, (D. Larhammar, B. Servenius, L. Rask and P. A. Peterson, "Characterization of an HLA DRβ Pseudogene", *Proc. Natl. Acad. Sci, USA*, 82, 1475–1479, (1985)). The pseudogene has stop codons in exon 2, reading frame mutations in exon 3, and an Alu type I repeat sequence located after exon 4. Furthermore, it is located on a Bam HI fragment of approximately 5.8 kb. In contrast, λ5.0, 4.0 and 4.3 do not contain stop, coding, or reading frame mutations (FIG. 3); they do not have an Alu type I sequence located after exon 4 (FIGS. 1 and 2), and they are located on Bam HI fragments of a different size. It thus seems plausible that λDR. 5.0, 4.0 and 4.3 are parts of expressed genes, although this has not been directly determined.

Most of the nucleotide sequence variability of the exon regions is located in exon 2, while less occurs in exon 3 and hardly any in exon 4 (FIG. 2). Sequence variability in the intervening regions is fairly uniform among the three genes, and these sequences have approximately 90% homology.

FIG. 3 shows the predicted amino acid sequences from the exon regions of λDR. 5.0, 4.3 and 4.0 and the published amino acid sequences of five DR B-chain proteins. The published sequences are 2918.4 from a homozygous DR1/1 cell line (Bell et al, 1985, supra), DRβ-1 from a DR4/6 cell line (Long et al, 9183), pII-β-3 and pII-β-4 from a DR3/6 cell line (Gustafsson and Wiman et al, 1984, supra), and DR2/2 from a DR2/2 cell line, (L. E. Walker, R. Hewick, M. N. Hunkapiller. L. E. Hood, W. J. Dreyer and R. A. Resifeld, *Biochemistry*, 22, 185–188, 1983)). It is noted that much of the amino acid variability is clustered around positions 9–13 and 26–33 of the amino terminal domain.

The sequences in FIG. 3 are compared with published DRB protein sequences: DRβ-1 (DR4/6 cell line; Long et al, 1983, supra), pII-β-3 and pII-β-4 (DR3/6 cell line; Gustafsson and Wiman et al, 1984, supra), and DR2/2 cell line; Walker et al, 1983, supra. Amino acids 5, 95, 189, 226 are circled and indicate the exon/intron boundaries. The first 5 amino acids and last 12 amino acids present in exons 1 and 5, respectively, were not determined in DR 5.0, 4.3 and 4.0. Sequences are compared with DR 5.0 and the differences shown.

The sequences (both nucleotide and amino acid) of pII-β-3 and λDR 4.0 are identical. Since pII-β-3 was isolated from a DR3/6 cell line and λDR 4.0 from a DR3/4 individual, λDR 4.0 and pII-β-3 appear to be associated with DR 3, λDR 5.0 and λDR 4.3 differ at multiple positions from all the published sequences (FIG. 3). From these genes DNA probes were constructed.

EXAMPLE 2

DNA Sequence Analysis

Using the restriction maps shown in FIG. 1, the Hind III fragments containing exon 2 and the Hind III-Bam HI fragments containing exons 3 and 4 were isolated by preparative gel electrophoresis on 1% agarose gels. The fragments were then cut out of the gel, electroluted into dialysis tubing, concentrated using 2-butanol and cleansed of agarose contamination by phenol and chloroform extractions and ethanol precipitation. Subsequently, the fragments containing exon 2 were digested with Hpa II (all enzymes were purchased from Boehringer, Mannheim, Federal Republic of Germany) and cloned into the Acc I site of bacteriophage MP-10 and bacteriophage MP-11 (New England Biolabs, Bethesda, Md.) using T₄ DNA ligase. Exons 3 and 4 were contained within a Hind III-Bam HI fragments of 1.9 kb. This fragment was isolated, and the Hind III, Pst I, Xba I and Bam HI sites (FIG. 1) were used to clone Hind III-Pst I, Pst I-Xba I, Xba I-Xba I, and Xba I-Bam HI fragments into MP-10 and MP-11. In the case of λDR 5.0, an additional digestion with Hpa II was necessary to complete the sequence. Sequencing was done using universal M13 primers and the dideoxy sequencing method of F. Sanger, S. Nicken and A. Coulsen, "DNA Sequencing With Chain-Terminating Inhibitors", *Proc. Natl. Sci. Acad. U.S.A.*, 74, 5463–5467, (1977). The sequences generated were analyzed using a Harris 500 computer and a Pustell Program for DNA sequence analysis (J. Pustell and F. C. Kafatos, "A Convenient and Adaptable Package of Computer Programs for DNA Protein Sequence Management, Analysis and Homology Determination", *Nucleic Acids Res.*, 14, 643–655, (1984)).

EXAMPLE 3

Southern Blot Analysis

Blood donor DNA was prepared by using lymphocytes from HLA-DR3/4 individuals. Such DNA was digested with Bam HI as previously described (Owerbach et al, 1983, supra). After gel electrophoresis, the DNA was transferred to Zetabind filters (AMF Corp.) by electroblotting using a procedure supplied by the manufacturer.

A probe-spanning nucleotide (1096–1882) of λDR 5.0 was used in the subsequent hybridization studies. The Xba I-Bam HI fragment (FIG. 1) was subcloned into pUC-13 and isolated by preparative gel electrophoresis. This fragment was then digested with Rsa I, and the Rsa I-Bam HI fragment was isolated by gel electrophoresis and labeled by nick translation (Maniatis et al, 1982, supra) using $^{32}$P-deoxycytidine triphosphate to specific activities of more than $10^8$ cpm/μg.

The filters were prehybridized and hybridized with the probe as described by Owebach et al, 1983, supra. The washing of the filters was preformed 3 times with 2× standard sodium citrate SSC at room temperature for 10 minutes per wash, followed by two 40 minutes washes in 0.1×SSC, 0.1% sodium dodecyl sulfate at 60° C. Autoradiographic exposures were for 3 to 7 days.

The Southern blot analysis was used to determine whether the Bam HI 5.0, 4.3 and 4.0 kb sequences are polymorphic in population and whether they differ between HLA-DR3/4 diabetic patients using a probe that includes exon 4 and flanking sequences (85% of the probe is from intervening sequences). The probe appeared to be specific for DRβ sequences and did not cross-hybridize with DQβ sequences under the conditions utilized. FIG. 9B shows the results of Southern blot analysis on blood donor DNAs. A total of nine restriction fragments were detected using Bam HI (4.0, 4.3, 4.4, 5.0, 5.1, 5.8, 7.0, 10.0 and 12.0 kb); and all but the 10.0 kb fragment were polymorphic (26 individuals were examined). FIG. 9A shows the results of Southern blot analysis performed on HLA-DR3/4 individuals. In total, 11 HLA-DR3/4 healthy controls and 12 HLA-DR3/4 IDDM patients were analyzed. All contained polymorphic 4.3, 4.4, 5.0, 5.8, 7.0 and 12.0 kb sequences (Bam HI) and all but two IDDM patients contained the 4.0 kb sequence. The 4.0, 4.3 and 5.0 kb sequences appeared to present in λDR 5.0, 4.3 and 4.0. Furthermore, the 5.8 kb sequence is similar in size to a Bam HI fragment containing exon 4 in a DRβ pseudogene (Larhammar et al, 1983, supra).

Although the sizes of Bam HI restriction fragments that differentiated HLA-DR3/4 diabetics from controls could not be detected (FIG. 9A) there appeared to be sequence variation in restriction fragments of the same size. For example, the 5.0 kb restriction fragments showed a much higher degree of hybridization intensity in some individuals (FIG. 4A, lane 2). While only 1 out of 23 HLA-DR3/4 individuals from the United States or England had this stronger signal; the frequency of this sequence seems to be higher in Scandinavia. Indeed, the probe was derived from a Swedish patient and in control experiments using cloned λDR 5.0, λDR 4.3 and λ4.0 DNA, the probe hybridized much more strongly to the homologous DR 5.0 sequences. When the probe was used to test eight HLA-DR3/4 Scandinavian IDDM patients and five HLA-DR3/4 Scandinavian healthy individuals (Owerbach et al, 1983, supra), the five controls showed strong hybridization at 5.0 kb, but hybridization was greatly reduced in all eight IDDM patients. It thus appears likely that the strongly hybridizing 5.0 kb Bam HI sequence in the Scandinavian population exists in linkage disequilibrium with DR3 or DR4, but not with IDDM susceptibility.

EXAMPLE 4

Two probes, A (RsaI fragment) from λDR 5.0 and B (XbaI fragment) from λDR 4.0 were isolated and their sequence is shown in FIG. 4. The probes contain intervening sequences located between Exons 3 and 4 respectively, see (FIG. 1). Probe A contains 144 bp and differs from related sequences in λDR 4.0 at 17 of positions (88% homology). Probe B contains 269 bp and differs from the homologous region of λDR 5.0 at 26 positions (90% homology). The positions which show mismatch are underlined. The relatively small size of these probes along with mismatches distributed along much of the sequence, allows detection of highly homologous sequences by differential hybridization and washing conditions.

EXAMPLE 5

Probes A and B of Example 4 were labelled with $^{32}P$ and used to study DNA isolated from 9 HLA-DR3/4 healthy controls and 8 HLA-DR matched IDDM patients. The human DNA was digested with Bam HI and EcoRI together, and resulting fragments were separated by slab gel electrophoresis and subjected to the Southern hybridization technique. An autoradiogram of the detected sequences is shown in FIG. 5. Sequences were detected in some individuals at 2.0, 2.5 and/or 5.0 kilobases (kb). However, while the intensity of the signals at 2.0, 2.5 and 5.0 kb were approximately equal with probe B, they show a dramatically differential hybridization in some individuals with probe A (i.e., lanes 2 and 5 to 9). Lanes 1 to 9 were from HLA-DR3/4 controls and lanes 10 to 17 were from HLA-DR3/4 IDDM patients. While all were identical by HLA-DR typing, 6 out of 9 of the non-diabetics were distinguishable from the 8 IDDM patients. Therefore, the liability to develop IDDM is low in individuals containing the strongly hybridizing sequence with probe B.

EXAMPLE 6

The sequence of Exon 2 which codes for the hypervariable amino terminal domain was determined in two DQ beta and three DR beta genes isolated from a HLA-DR3/4 IDDM patient. These sequences are shown in FIG. 6. Underlined therein are regions of exon 2 in which oligonucleotide probes of 17 to 19 nucleotides in length were prepared.

EXAMPLE 7

The sequence of DRB-1 (prepared from λDR 5.0 sequence) and DRβ-2 (prepared from λDR 4.0 sequence) differ from each other at 8 of 19 positions (FIG. 7). These sequences differ even more greatly from the corresponding regions of DQ beta and DR beta genes (FIG. 7). The DRβ-1 and DRβ-2 sequences were labelled with $^{32}P$ by end labelling with $\gamma$-$^{32}$-P-dATP using standard conditions. Cloned DNA containing exon 2 was bound directly to filters and hybridized (a dot blot assay). DRβ-1 probe hybridized specifically to DRβ-1 sequences, while DRβ-2 hybridized specifically to DQβ-2 sequences (FIG. 7). The use of other oligonucleotide probes of this size (not to HLA-D region genes) have been used to determine individuals having a proclivity to develop Sickle-Cell Anemia (Connor et al, *PNAS*, 80, 278-282, (1983)). However, without knowing the sequence of HLA-D genes of diabetic individuals, it was not possible to derive the appropriate sequences to make the oligonucleotide probes for this disease.

EXAMPLE 8

A DQ beta gene was isolated from a IDDM patient (see FIG. 8). The exon regions (1 to 5) contain sequence information found in the messenger RNA found in the cytoplasm of cells. The regions between the exons are called intervening sequences. Two DNA probes were made. Probe A is a 1.3 kb Hind III fragment which contains exon 2 and flanking sequences. Probe B is a 2.0 kb Taql fragment flanking exon 5 of the gene.

EXAMPLE 9

DQβ probes A and B of Example 8 were labeled with $^{32}P$ and used to study DNA isolated from blood donors and diabetic individuals. The human DNA was digested with Bam HI (A) or Taql (B) and resulting fragments were separated by slab gel electrophoresis and subjected to the Southern hybridization technique. An autoradiogram of detected sequences is shown in FIG. 9. FIG. 9 shows a Southern blot analysis of HLA-DR3/4 patients and blood donor DNAs. FIG. 9A: HLA-DR3/4 individuals: 1 and 2, IDDM patients; 3-10, healthy control subjects. FIG. 9B: Lanes 1-5 blood donor DNAs. DNA digested with Hind III (Boehringer, Mannheim, Federal Republic of Germany) was used as a molecular mass standard. Molecular masses are indicated in kb. With DQ probe A, sequences were detected at 3.0, 3.2, 3.4, 3.7, 4.0, 10.0 and 12.0 kb and with probe B, sequences were detected at 2.0, 2.3, 2.6, 3.0, 5.0 and 7.0 kb. These results are in contrast to DQβ cDNA probes used in the past because these cDNA probes are not specific for DQβ sequences and detect DRβ and DPβ sequences, as well. Furthermore, the differential degree of hybridization of the 10 kb sequences versus the 12 kb (A) or 5.0 kb versus 3.0 kb (B) is noted. The 10 kb Bam HI sequences and 3.0 kb Taql sequence hybridize more weakly to the probes than the other sequences and are derived from a second DQβ related gene. Therefore, these probes can differentiate individual DQβ genes though hybridization intensity, in addition to the more distantly related DRβ and DPβ beta genes. The combination of 12.0 and 4.0 kb Bam HI sequences (probe DQ A), in addition to 2.0 and 5.0 kb Taql sequences (probe DQ B), are common to IDDM patients, but rare in the general population: 12/12 HLA-DR3/4 IDDM patients versus 2/80 random control individuals (the IDDM population is composed of approximately 50% HLA-DR3/4 individuals). Therefore, individuals containing the Bam HI 12 and 4.0 kb sequences with probe A, in addition to Taql 2.0 and 5.0 with DQ probe B, are at high risk for developing IDDM. This typing is better than conducting HLA-DR typing alone since not all HLA-DR3/4 healthy individuals contain the DNA sequences specified by the above probes. In addition; some non-HLA-DR3/4 individuals contain these sequences as well.

EXAMPLE 10

DNA from 27 families consisting of 31 IDDM patients and 68 non-diabetic siblings using oligonucleotide probes are tested. The DNA is amplified using the polymerase chain reaction (PCR) of Saiki, R. K., et al, *Nature*, 324, 163-166, (1986) and is then applied to a nylon membrane filter. The filter is then hybridized with $^{32}P$-labeled oligonucleotide probe. The probes are based on sequences GAGAGGAGTACGCACGCTT, GAGAAGAGATCGTGCGCTT, and CGTGCGTCTTGTGACCAGA which are from Exon 2 sequences of DQβ genes associated with DR3 or DR4 from a IDDM patient (see FIG. 6). The key amino acids coded by the oligonucleotide sequences used in the probes reside around amino acid residues DQβ-26, 37 and 38.

Additional oligonucleotide probes which correspond to published sequences of non-diabetic individuals which differentiate [26]Tyr (Michelson, B. and Lernmark, A., *J. Clin. Invest.*, 1144–1152, 1987) and [26]Gly (Turco et al, *Immunogenetics*, 26, 282–240, 1987) were synthesized. Using the oligonucleotide probes in diabetic individuals and their non-diabetic siblings the DQβ genes having [26]Gly, [37]Ile and [38]Val are present more frequently in the diabetics, while [26]Tyr is found more frequently in the non-diabetic siblings. Thus oligonucleotide probes of the invention are stronger predictors of diabetes than previously available probes.

Todd et al, *Nature*, 329, 599–604, Oct. 15, 1987 further demonstrate the importance of [57]Ala which is frequently found in diabetic individuals having DR3 and DR4 and which are specified by probes GGCCGCCTGCCGCCGAG and GCTGGGGCTGCCTGCCG and are underlined in FIG. 6.

It will be appreciated that the instant specification and examples are set forth by way of illustration and not limitation, and that various modifications and changes may be made without departing from the spirit and scope of the present invention.

What is claimed is:

1. A DQ beta gene oligonucleotide consisting essentially of a nucleotide with in oligonucleotide with the sequence GGCCGCCTGCCGCCGAG.

2. A method of assaying for a polymorphic region associated with Type I diabetes mellitus in humans, the method comprising
   (a) isolating a sample containing genomic or chromosomal DNA from a human,
   (b) transferring the isolated DNA from step (a) to a substance that binds DNA,
   (c) contacting the resultant DNA bound to the substance from step (b) under hybridization conditions with a labelled DQ beta gene oligonucleotide, said oligonucleotide being GGCCGCCTGCCGCCGAG and
   (d) conducting detection for the label.

* * * * *